United States Patent [19]

Langlois et al.

[11] 4,346,102

[45] Aug. 24, 1982

[54] 3H-DIHYDROFURANONE-2 DERIVATIVES AND PHARMACEUTICAL USE THEREOF

[75] Inventors: Michel Langlois, Buc; Alain P. Lacour, La Varenne; Bernard P. Bucher, Marnes la Coquette; Gisèle C. Mocquet, Paris, all of France

[73] Assignee: Delalande S.A., Courbevoie, France

[21] Appl. No.: 144,075

[22] Filed: Apr. 28, 1980

[30] Foreign Application Priority Data

May 7, 1979 [FR] France ............................. 79 11453

[51] Int. Cl.³ .................. C07D 307/32; C07D 405/12; A61K 31/365; A61K 31/44

[52] U.S. Cl. ................................ 424/279; 424/263; 546/283; 549/323

[58] Field of Search .................... 260/343.6; 546/283; 424/279, 263

Primary Examiner—Norma S. Milestone
Attorney, Agent, or Firm—Blanchard, Flynn, Thiel, Boutell & Tanis

[57] ABSTRACT

Derivatives of 5H-furanone-2 and 3H-dihydrofuranone-2, substituted at the 3 position with substituted phenyl and at the 5 position with substituted methyl, are prepared by various processes. The derivatives are inhibitors of monoamine oxidase and are useful for treating depression.

9 Claims, No Drawings

3H-DIHYDROFURANONE-2 DERIVATIVES AND PHARMACEUTICAL USE THEREOF

The present invention relates to new derivatives of 5H-furanone-2 and 3H-dihydrofuranone-2, the process for preparing same and the application thereof in therapeutics.

It will be noted that the derivatives of 3H-dihydrofuranone-2 have two asymmetrical carbon atoms and are therefore formed of a mixture of four diastereoisomers. Therefore, the applicant has subjected each derivative of 3H-dihydrofuranone-2 to chromatographic treatment, which in some cases allowed it to be separated into two products corresponding in fact to the same formula but each corresponding to a pair of diastereoisomers.

In the following description and in the claims, the isolated products having a "trans" (the least polar) structure will be characterized by the letter A and the isolated products having a "cis" (the most polar) structure will be characterized by the letter B, this stereochemistry having been determined:

on the one hand, by identification of the most polar products with products obtained by hydrogenation of the corresponding 5H-furanones-2, and on the other hand, by analogy with the work of W. David OLLIS et al. described in J. Chem. Soc. Perkin I, 1975, 1480.

Finally, the derivatives of 3H-dihydrofuranone-2 defined without any other mention correspond to a mixture of the four diastereoisomers.

More precisely, the new derivatives of the present invention correspond to the general formula:

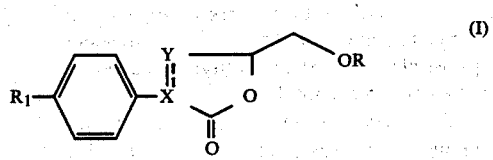

in which:

R represents a hydrogen atom in which case —X═Y— represents the chain —CH—CH$_2$— and R$_1$ represents one of the following groups: 3-methylbutoxy, cyclohexylmethoxy, metanitrobenzyloxy, metanitrobenzyloxy A, metanitrobenzyloxy B, metcyanobenzyloxy and 3-cyano-5-nitrobenzyloxy;

R represents the acetyl group in which case —X═Y— represents the chain —CH—CH$_2$— and R$_1$ represents the metanitrobenzyloxy A or metanitrobenzyloxy B group, or R represents the methyl group in which case:

either —X═Y— represents the chain —CH—CH$_2$—, R$_1$ then representing one of the following groups: 4-chlorobutoxy, 4-chlorobutoxy B, 4-cyanobutoxy, benzyloxy, benzyloxy B, metanitrobenzyloxy, metanitrobenxyloxy A, metanitrobenzyloxy B, metachlorobenzyloxy, metachlorobenzyloxy A, metachlorobenzyloxy B, metacyanobenzyloxy, metacyanobenzyloxy A, metacyanobenzyloxy B, 3-methoxypyridine, 3-cyano-5-nitrobenzyloxy, 3-cyano-5-nitrobenzyloxy A, 3-cyano-5-nitrobenzyloxy B, 3-chloro-4-fluorobenzyloxy, 3-chloro-4-fluorobenzyloxy A, 3-chloro-4-fluorobenzyloxy B;

or —X═Y— represents the chain —C═CH—, R$_1$ then representing one of the following groups: metanitrobenzyloxy, metachlorobenzyloxy, metacyanobenzyloxy, benzyloxy, 3-chloro-4-fluorobenzyloxy.

The process of the invention for preparing the compounds of formula (I) in which R represents a hydrogen atom consists in condensing on the compound of formula (II)A, (II) B or (II) A+B:

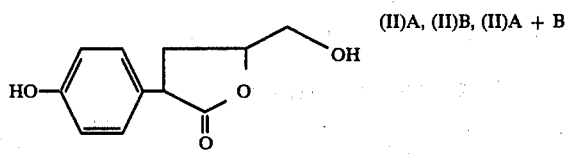

the halogenides of formula:

R$_2$—Z in which Z represents a chlorine or bromine atom and R$_2$ represents the group 3-methylbutyl, cyclohexylmethyl, metanitrobenzyl, metacyanobenzyl or 3-cyano-5-nitrobenzyl.

This condensation is preferably carried out to reflux in acetonitrile in the presence of potassium carbonate.

The compounds of formula (I) thus obtained are subjected to thin layer chromatography. When this latter allows two pair of diastereoisomers (I) A and (I) B to be distinguished, these latter are separated by high performance liquid chromatography (H.P.L.C.).

The above compound of formula (II) A, (II) B or (II) A+B is new and is obtained by treating, with 48% bromhydric acid, a compound of formula (III) A or (III) B or a mixture of the compounds of formula (III) A and (III) B, or else the compound of formula (IV):

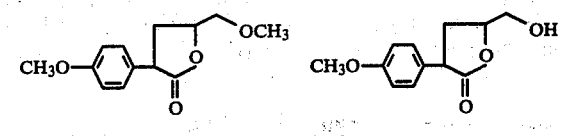

The compounds of formula (III) A, (III) B or (III) A+B, also new, are obtained by a multi-step synthesis which consists in condensing paramethoxyphenylacetic acid of formula (V):

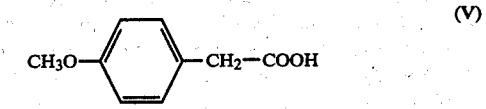

with 1,2-epoxy-3-methoxypropane of formula (VI):

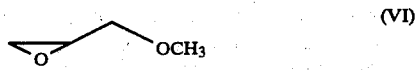

to reflux in tetrahydrofuran in the presence of naphthalene-lithium and diethylamine, then in treating the raw reaction product with an aqueous solution of hydrochloric acid. The raw product thus obtained is then dissolved in benzene and the solution is brought to reflux until no more water is eliminated. Finally, the compound obtained is chromatographed by H.P.L.C.

The new compound (IV) is obtained by condensation of paramethoxyphenylacetic acid ethyl ester of formula (VII):

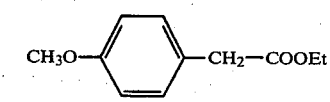
(VII)

with 1,3-dioxolan of formula (VIII):

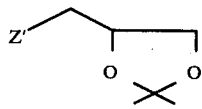
(VIII)

in which Z' represents the bromine atom or a paratoluenesulfonyloxy or methylsulfonyloxy group.

Condensation is preferably carried out to reflux in dimethylformamide in the presence of sodium hydride, then the raw reaction product is treated at reflux in an 80-20 acetic acid and water mixture.

The process of the invention for preparing compounds of formula (I) in which R represents the acetyl group consists in condensing the compounds of formula (I) A and (I) B in which R represents hydrogen atom, —X═Y— represents the chain —CH—CH$_2$— and R$_1$ represents the metanitrobenzyloxy group, with acetyl chloride, in the presence of triethylamine in a tetrahydrofuranic medium.

The process of the invention for preparing the compounds of formula (I) in which R represents the methyl group and —X═Y— represents the chain —CH—CH$_2$—, with the exception of the one where R$_1$ is benzyloxy or benzyloxy B group, consists in condensing the compound of formula (IX):

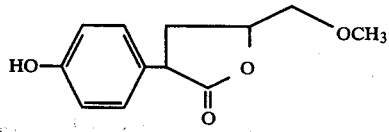
(IX)

with halogenides of formula R$_3$—Z in which Z represents a chlorine or bromine atom and R$_3$ represents 4-chlorobutyl, 4-cyanobutyl, metanitrobenzyl, metachlorobenzyl, metacyanobenzyl, 3-methylpyridine, 3-cyano-5-nitrobenzyl, or 3-chloro-4-fluorobenzyl group.

Condensation is preferably carried out to reflux in acetonitrile in the presence of a base such as potassium carbonate.

When the study by thin layer chromatography of the compounds of formula (I) thus obtained allows two pairs of diastereoisomers (I) A and (I) B to be distinguished, these latter are separated by H.P.L.C. For the compounds of formula (I) in which R$_1$ represents the 4-chlorobutoxy and benzyloxy groups, only the identified fraction B was collected.

The new compound of formula (IX) is obtained by hydrogenolysis in the presence of palladium on charcoal, in a methanol solution of the compound of formula (I) in which R represents the methyl group, —X═Y— represents the chain —CH—CH$_2$— and R$_1$ represents the benzyloxy group, and represented by the following developed formula (X):

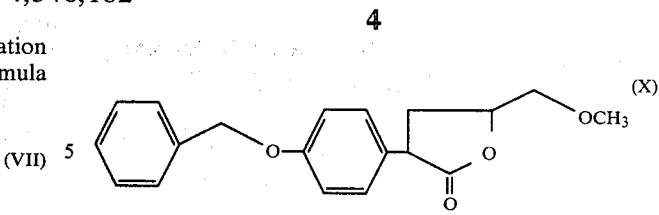
(X)

This compound, also new, is obtained from parabenzyloxyphenylacetic acid of formula (XI):

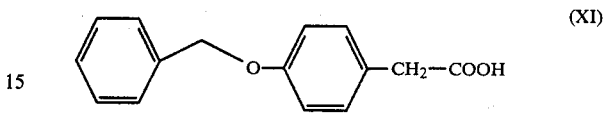
(XI)

by a process identical to that used in the synthesis of the compound of formula (III).

The process of the invention for preparing the compounds of formula (I) in which R represents the methyl group and —X═Y— represents the chain —C═CH— consists in condensing the compound of formula (XII):

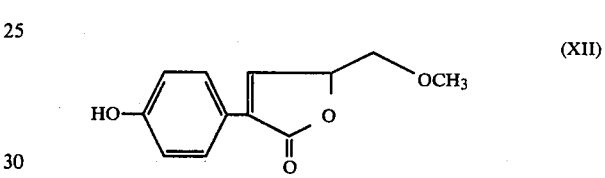
(XII)

with alcohols of formula R$_4$—OH, in which R$_4$ represents the metacyanobenzyl, metachlorobenzyl, metanitrobenzyl, benzyl and 3-chloro-4-fluorobenzyl groups.

This condensation is preferably carried out in a tetrahydrofuranic medium, in the presence of triphenyl phosphine (P $\phi_3$) and ethyl diazadicarboxylate (EtO—CO—N═N—COOEt).

The new compound (XII) is obtained by simultaneous debenzoylation and debromhydratation, by means of hydrochloric acid methanol solution, of the compound of formula (XIII):

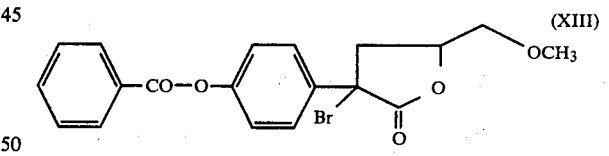
(XIII)

Compound (XIII), also new, is obtained by treating with N-bromosuccinimide (N.B.S.), in the presence of benzoyl peroxide in solution in carbon tetrachloride, the compound of formula (XIV):

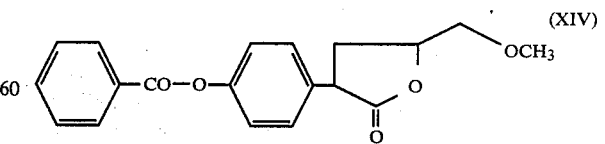
(XIV)

itself new and obtained by condensing the compound of formula (IX) with benzoyl chloride, in a tetrahydrofuranic medium, in the presence of triethylamine.

The following preparations are given by way of example to illustrate the invention.

EXAMPLE 1:
3-para(metanitrobenzyloxy)phenyl-5-hydroxymethyl-3H-dihydrofuranone-2 (I)

Code number: 6, 6 A and 6 B

1st. stage:
3-paramethoxyphenyl-5-methoxymethyl-3H-dihydrofuranone-2 (III), (III) A and (III) B.

To a solution of 12.8 g of naphthalene in 100 ml of tetrahydrofuran was added 1.4 g of lithium, and they were left in contact at ambient temperature for two hours, then 14.6 g of diethylamine were added and the whole agitated until the lithium had disappeared. A solution of 16.6 g of paramethoxy phenylacetic acid (V) in 30 ml of tetrahydrofuran was added then, after 30 min., a solution of 8.8 g of 1,2-epoxy-3-methoxypropane (VI) was slowly added and the mixture was brought to reflux for 4 hours. Then it was thrown in a mixture of ice and aqueous NaOH, the aqueous phase was washed with isopropyl ether, acidified by means of concentrated hydrochloric acid and extracted with ethyl acetate. The organic phase was dried on sodium sulfate, the solvent evaporated and the raw product obtained dissolved in 100 ml of benzene. The solution was brought to reflux while eliminating the water formed, then cooled, washed with an aqueous solution of sodium bicarbonate, dried on sodium sulfate, and the solvent was evaporated. 18 g (76% yield) of oily compound (III) was obtained, which was chromatographed by H.P.L.C. ($SiO_2$ 12–25$\mu$) (eluent 50/50 ethylacetate-heptane). Thus 7.1 g of oily compound (III) A were obtained.

Yield: 30%
Empirical formula: $C_{13}H_{16}O_4$

| . Elementary analysis: | C | H |
|---|---|---|
| Calculated (%) | 66;08 | 6;83 |
| Obtained (%) | 66;21 | 6;99 | and 7.4 g of oily compound (III) B
Yield: 32%
Empirical formula: $C_{13}H_{16}O_4$

| . Elementary analysis: | C | H |
|---|---|---|
| Calculated (%) | 66;08 | 6;83 |
| Obtained (%) | 65;90 | 6;58 |

2nd stage:
3-parahydroxyphenyl-5-hydroxymethyl-3H-dihydrofuranone-2 (II)

A solution of 0.7 g of compound (III), obtained in the preceding step, in 7 ml of 48% bromhydric acid was brought to reflux for an hour, then 20 ml of water and 20 ml of a saturated aqueous solution of sodium chloride and 50 ml of ethyl acetate were added. It was neutralized with an aqueous solution of bicarbonate of sodium, the organic phase was decanted, dried on sodium sulfate and evaporated. 0.5 g (yield 81%) of compound (II) was obtained; it was crystallized in ethyl acetate:

Melting point: 120° C.
IR spectrum: phenol and alcohol bands at 3440 and 3240 $cm^{-1}$ lactone band 1730 $cm^{-1}$
NMR spectrum (DMSO) $\delta$ ppm: 9.65, s, 1 phenol proton 7.04, d, and 6.67, d, (J=9 Hz): 4 benzene protons centred on 5.03, m, 1H in position-5 of the furanone ring centred on 4.58, m, 1H in position-3 of the furanone ring centred on 3.88, t, 2 methyl protons of the hydroxymethyl-5 group centred on 2.42, m, 2 protons in position 4 of the furanone ring 3.62, s, —OH

3rd stage: 3-para(metanitrobenzyloxy) phenyl-5-hydroxymethyl-3H-dihydrofuranone-2 (I), code number: 6, 6A and 6 B A mixture of 25.8 g of compound (II) obtained in the preceding stage, 21.2 g of metanitrotoluene chloride and 49.6 g of potassium carbonate in 150 ml of acetonitrile was brought to reflux for 4 hours, then filtered, the solvent was evaporated, and the residue crystallized in a mixture of ethyl acetate and n-heptane (80–20). Thus was obtained the mixture of the four diastereoisomers of code number 6 appearing in table I, which was chromatographed by H.P.L.C. (eluent ethyl acetate 80 n-heptane 20). 11 g. of compound (I)A of code number 6 A were obtained.

Yield: 25%
Melting point: 98° C.
Empirical formula: $C_{18}H_{17}NO_6$

| . Elementary analysis: | C | H | N |
|---|---|---|---|
| Calculated (%) | 62;97 | 4;99 | 4;08 |
| Obtained (%) | 62;67 | 5;09 | 3;80 | and 12 g of compound (I) B, code number: 6 B.
Yield: 30%
Melting point: 115° C.
Empirical formula: $C_{18}H_{17}NO_6$

| . Elementary analysis: | C | H | N |
|---|---|---|---|
| Calculated (%) | 62;97 | 4;99 | 4;08 |
| Obtained (%) | 62;46 | 5;21 | 4;15 |

By the same process, but from the corresponding reagents, there were obtained the compounds of formula (I), appearing in table I below and having the code numbers: 1, 2, 12 and 16.

EXAMPLE 2:
3-parahydroxyphenyl-5-hydroxymethyl-3H-dihydrofuranone-2 (II)

1st stage: paramethoxyphenyl-3 hydroxymethyl-5 3H-dihydrofuranone-2 (IV)

To a solution of 40.8 g of paramethoxyphenylacetic acid ethyl ester (VII) and 60 g of 4-paratosyloxymethyl-2,2-dimethyl-1,3-dioxolane (VIII), in 300 ml of dimethylformamide, and in an argon atmosphere, were added 10 g of sodium hydride, then the solution was brought to 60° C. to initiate the reaction, then for 5 hours at 90° C. The solution was diluted with 300 ml of water, extracted with ethyl acetate, the solvent was evaporated and the residue distilled ($Eb_{0.1}$=158°–160° C.). The product obtained was added to an acetic acid-water mixture (80–20) and the solution was brought to reflux for 45 minutes then diluted with iced water, and the pH of the solution was brought up to 6 with sodium bicarbonate, the product was extracted with ethyl acetate, dried on sodium sulfate and the solvent was evaporated. 13 g of an oil was obtained which crystallized slowly.

Yield: 56%
Melting point: <50° C.

Empirical formula: $C_{12}H_{14}O_4$

| . Elementary analysis: | C | H |
| --- | --- | --- |
| Calculated (%) | 64;85 | 6;35 |
| Obtained (%) | 64;61 | 6;03 |

2nd stage:
3-parahydroxyphenyl-5-hydroxymethyl-3H-dihydrofuranone-2 (II)

The process was identical to the one used in the 2nd stage of example 1, but from the preceding compound (IV).

EXAMPLE 3: 3-para(metanitrobenzyloxy) phenyl-5-acetoxymethyl-3H-dihydrofuranone-2 (I), code numbers: 7 A and 7 B.

To a solution cooled to 5° C. of 3.4 g of 3-para(-metanitrobenzyloxy)phenyl-5-hydroxymethyl-3H-dihydrofuranone-2 (I), 6 A, described in example 1, in 100 ml of tetrahydrofuran, were added 1.5 g of acetyl chloride then 2 g of triethylamine, the residue was taken up in ethyl acetate, washed with water, dried on sodium sulfate, the solvent evaporated and the residue crystallized in ether. 3 g of compound 7 A were obtained.
Yield: 79%
Melting point: 78° C.
Empirical formula: $C_{20}H_{19}NO_7$

| . Elementary analysis: | C | H | N |
| --- | --- | --- | --- |
| Calculated (%) | 62;33 | 4;97 | 3;64 |
| Obtained (%) | 62;47 | 5;08 | 3;48 |

By the same process, but from compound (I) 6 B, described in example 1, compound (I) 7 B was obtained.
Yield: 89%
Melting point: 108° C.
Empirical formula: $C_{20}H_{19}NO_7$

| . Elementary analysis: | C | H | N |
| --- | --- | --- | --- |
| Calculated (%) | 62;33 | 4;97 | 3;64 |
| Obtained (%) | 62;25 | 4;92 | 3;53 |

EXAMPLE 4: 3-para(metanitrobenzyloxy) phenyl-5-methoxymethyl-3H-dihydrofuranone-2 (I), code numbers: 8, 8 A and 8 B 1st stage:
3-parabenzyloxyphenyl-5-methoxymethyl-3H-dihydrofuranone-2 (X)

The process used is identical to the one used in the synthesis of compound (III) described in the 1st stage of example 1, but from parabenzyloxyphenylacetic acid (XI). 65% of compound (X) were obtained.
Melting point: 124° C.
Empirical formula: $C_{19}H_{20}O_4$

| . Elementary analysis: | C | H |
| --- | --- | --- |
| Calculated (%) | 73;06 | 6;45 |
| Obtained (%) | 73;02 | 6;47 |

2nd stage:
3-parahydroxyphenyl-5-methoxymethyl-3H-dihydrofuranone-2 (IX)

A suspension of 43 g of compound (X) obtained in the preceding stage and 4.3 g of palladium on charcoal (10%) in 700 ml of methanol was hydrogenolyzed for 2 hours at a pressure of 5 bars of hydrogen. Then it was filtered and the solvent evaporated. 26 g of product were obtained.
Yield: 87%
Melting point: 75° C.
Empirical formula: $C_{12}H_{14}O_4$

| . Elementary analysis: | C | H |
| --- | --- | --- |
| Calculated (%) | 64;85 | 6;35 |
| Obtained (%) | 64.58 | 6;69 |

3rd stage: 3-para(metanitrobenzyloxy) phenyl-5-methoxymethyl-3H-dihydrofuranone-2 (I) code numbers: 8, 8 A and 8 B.

The process used is identical to the one used in the 3rd stage of example 1, but from compound (IX). Thus was obtained a product of code number 8 which, subjected to separation by H.P.L.C. (eluent ethyl acetate 70-n-heptane 30), gave 23% of compound (I) A [8 A].
Melting point: 78° C.
Empirical formula: $C_{19}H_{19}NO_6$

| . Elementary analysis: | C | H | N |
| --- | --- | --- | --- |
| Calculated (%) | 63;86 | 5;36 | 3;92 |
| Obtained (%) | 63;63 | 5;06 | 3;73 | and 50% of compound (I) B [8 B].
Melting point: 56° C.
Empirical formula: $C_{19}H_{19}NO_6$

| . Elementary analysis: | C | H | N |
| --- | --- | --- | --- |
| Calculated (%) | 63;86 | 5;36 | 3;92 |
| Obtained (%) | 63;64 | 5;37 | 4;10 |

By the same process, but from the corresponding reagents the compounds (I) were obtained which appear in table I under code numbers 3, 3B, 4, 5, 5B, 10, 10A, 10B, 13, 13A, 13B, 15, 17, 17 A, 17 B, 18, 18 A and 18 B.

EXAMPLE 5: 3-para(metacyanobenzyloxy) phenyl-5-methoxymethyl-3H-furanone-2 (I), code number: 14

1st stage: (parabenzoyloxy) phenyl-3 methoxymethyl-5 3H-dihydrofuranone-2 (XIV)

To a solution of 1 g of 3-parahydroxyphenyl-5-methoxy methyl-3H-dihydrofuranone-2 (IX), described in the 2nd stage of example 4, in 25 ml of tetrahydrofuran were added 1.3 g of triethylamine then 0.7 g of benzoyl chloride. After 20 minutes at ambient temperature it was filtered, the filtrate was evaporated, the residue was taken up in ethyl acetate, washed with a saturated aqueous solution of sodium bicarbonate, dried on sodium sulfate, the solvent was evaporated and the residue crystallized was washed with ether.
Yield: 94%
Melting point: 108° C.

Empirical formula: $C_{19}H_{18}O_5$

| . Elementary analysis: | C | H |
|---|---|---|
| Calculated (%) | 69;93 | 5;56 |
| Obtained (%) | 69;89 | 5;68 |

2nd stage: 3-Bromo-3 (parabenzoyloxy) phenyl-5-methoxymethyl-3H-dihydrofuranone-2 (XIII)

A solution of 10 g of compound (XIV) obtained in the preceding stage, 5.4 g of N-Bromosuccinimide and a few crystals of benzoyl peroxide in 350 ml of carbon tetrachloride was brought to reflux for 3 hours. Then it was filtered, the filtrate evaporated and the residue crystallized in ether. 63% of compound (XIII) were obtained.
Melting point: 136° C.
Empirical formula: $C_{19}H_{17}BrO_5$

| . Elementary analysis: | C | H |
|---|---|---|
| Calculated (%) | 56;31 | 4;23 |
| Obtained (%) | 55;98 | 4;05 |

3rd stage: 3-parahydroxyphenyl-5-methoxymethyl-5H-furanone-2 (XII)

A solution of 10 g of compound (XIII) obtained in the preceding stage in 125 ml of methanol saturated with gaseous hydrochloric acid was brought to reflux for 4 hours. Then it was evaporated, the residue taken up in ethyl acetate, washed with an aqueous solution of sodium bicarbonate, dried on sodium sulfate and the solvent evaporated. The residue was crystallized in ether.
Yield: 67%
Melting point: 141° C.
Empirical formula: $C_{12}H_{12}O_4$

| . Elementary analysis: | C | H |
|---|---|---|
| Calculated (%) | 65;44 | 5;49 |
| Obtained (%) | 64;57 | 5;49 |

4th stage: 3-para(metacyanobenzyloxy)-phenyl-5-methoxymethyl-5H-furanone-2 (I) code number: 14

To a solution, swept by an argon stream and cooled to 0° C., of 2.2 g of compound (XII) obtained in the preceding stage, 3.1 g of triphenyl phosphine and 1.5 g of metacyanobenzyl alcohol in 60 ml of tetrahydrofuran, were added 2 g of ethyl diaza-dicarboxylate (DEADC) within 10 minutes. Then, it was left for 30 minutes at 0° C. and 90 minutes at ambient temperature, the solvents were evaporated, and the residue chromatographed on a silica column. After elimination of impurities by means of toluene, the chromatography was stopped and the product was extracted from the silica by means of a mixture of methylene chloride and methanol. The solvent was evaporated and the residue was recrystallized in ether.
Yield: 30%
Melting point: 70° C.
Empirical formula: $C_{20}H_{17}NO_4$

| . Elementary analysis: | C | H | N |
|---|---|---|---|
| Calculated (%) | 71;63 | 5;11 | 4;18 |
| Obtained (%) | 71;67 | 5;05 | 4;25 |

By the same process, but from the corresponding reagents, the compounds (I) appearing in table I under code numbers: 9, 11, 19 and 20 were obtained.

EXAMPLE 6:
3-para(metacyanobenzyloxy)-phenyl-5-methoxymethyl-3H-dihydrofuranone-2 (I) "cis", code number 13 B A solution of 0.5 g of compound (I) of code number 14, obtained in the preceding example 5, in 50 ml of anhydrous methanol was hydrogenated at 0° C. and at normal pressure in the presence of 0.05 g of palladium on charcoal. Then, after 80 minutes of reaction, it was filtered, the filtrate was evaporated and 90% of "cis" compound 13 B was obtained. This latter was identical, particularly in thin layer chromatography, to the compound obtained in example 4 (13 B) and appearing in table I. It was deduced therefrom that the most polar compound has a "cis" structure.

TABLE I

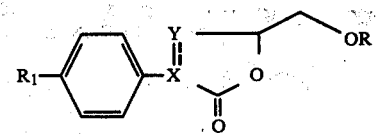

| Compound Code number | —X=Y— | —OR | —R₁ | Empirical formula | Molecular weight | Melting point (°C.) | Yield (%) | ELEMENTARY ANALYSIS | | |
|---|---|---|---|---|---|---|---|---|---|---|
| | | | | | | | | % | C | H | N |
| 1 | —CH—CH₂— | —OH | —O-CH₂CH(CH₃)₂ | $C_{16}H_{22}O_4$ | 278.34 | <50 | 83 | Cal. | 69.04 | 7.97 | — |
| | | | | | | | | Obt. | 68.50 | 7.99 | — |
| 2 | " | " | —O-CH₂-cyclohexyl | $C_{18}H_{24}O_4$ | 304.37 | 120 | 11 | Cal. | 71.02 | 7.95 | — |
| | | | | | | | | Obt. | 70.63 | 7.62 | — |
| 3 B | " | —OCH₃ | —O—(CH₂)₄—Cl | $C_{16}H_{21}ClO_4$ | 312.78 | 56 | 14 | Cal. | 61.44 | 6.77 | — |
| | | | | | | | | Obt. | 61.19 | 6.99 | — |
| 3 | " | " | " | " | " | — | — | Cal. | 61.44 | 6.77 | — |
| | | | | | | | | Obt. | — | — | — |
| 4 | " | " | —O—(CH₂)₄—CN | $C_{17}H_{21}NO_4$ | 303.35 | <50 | 48 | Cal. | 67.31 | 6.98 | 4.62 |

TABLE I-continued

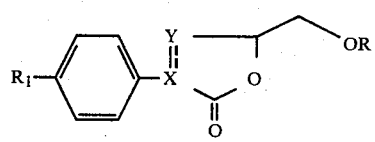

| Compound Code number | —X═Y— | —OR | —R₁ | Empirical formula | Molecular weight | Melting point (°C.) | Yield (%) | | ELEMENTARY ANALYSIS | | |
|---|---|---|---|---|---|---|---|---|---|---|---|
| | | | | | | | | % | C | H | N |
| | | | | | | | | Obt. | 67.17 | 6.87 | 4.32 |
| 5 B | " | " | —O—CH₂—C₆H₅ | C₁₉H₂₀O₄ | 312.35 | 130 | 21 | Cal. | 73.06 | 6.45 | — |
| | | | | | | | | Obt. | 73.31 | 6.59 | — |
| 5 | " | " | —O—CH₂—C₆H₅ | C₁₉H₂₀O₄ | " | — | — | Cal. | 73.06 | 6.45 | — |
| | | | | | | | | Obt. | — | — | — |
| 6 A | " | —OH | —O—CH₂—C₆H₄—NO₂ | C₁₈H₁₇NO₆ | 343.33 | 98 | 25 | Cal. | 62.97 | 4.99 | 4.08 |
| | | | | | | | | Obt. | 62.67 | 5.09 | 3.80 |
| 6 B | " | " | " | " | " | 115 | 30 | Cal. | 62.97 | 4.99 | 4.08 |
| | | | | | | | | Obt. | 62.56 | 5.21 | 4.15 |
| 6 | " | " | " | " | " | 110 | 60 | Cal. | 62.97 | 4.99 | 4.08 |
| | | | | | | | | Obt. | 62.68 | 5.17 | 4.27 |
| 7 A | " | —OCOCH₃ | " | C₂₀H₁₉NO₇ | 385.36 | 78 | 79 | Cal. | 62.33 | 4.97 | 3.64 |
| | | | | | | | | Obt. | 62.47 | 5.08 | 3.48 |
| 7 B | " | " | " | C₂₀H₁₉NO₇ | " | 108 | 89 | Cal. | 62.33 | 4.97 | 3.64 |
| | | | | | | | | Obt. | 62.25 | 4.92 | 3.53 |
| 8 A | " | —OCH₃ | " | C₁₉H₁₉NO₆ | 357.35 | 78 | 23 | Cal. | 63.86 | 5.36 | 3.92 |
| | | | | | | | | Obt. | 63.63 | 5.06 | 3.73 |
| 8 B | " | " | " | " | " | 56 | 50 | Cal. | 63.86 | 5.36 | 3.92 |
| | | | | | | | | Obt. | 63.84 | 5.37 | 4.10 |
| 8 | " | " | " | " | " | — | — | Cal. | 63.86 | 5.36 | 3.92 |
| | | | | | | | | Obt. | — | — | — |
| 9 | —C═CH— | " | " | C₁₉H₁₇NO₆ | 355.33 | 107 | 43 | Cal. | 64.22 | 4.82 | 3.94 |
| | | | | | | | | Obt. | 64.21 | 4.71 | 3.92 |
| 10 A | —CH—CH₂— | " | —O—CH₂—C₆H₄—Cl | C₁₉H₁₉ClO₄ | 346.80 | <50 | 16 | Cal. | 65.80 | 5.52 | — |
| | | | | | | | | Obt. | 65.86 | 5.53 | — |
| 10 B | " | " | " | " | " | 98 | 34 | Cal. | 65.80 | 5.52 | — |
| | | | | | | | | Obt. | 65.64 | 5.59 | — |
| 10 | " | " | " | " | " | — | — | Cal. | 65.80 | 5.52 | — |
| | | | | | | | | Obt. | — | — | — |
| 11 | —C═CH— | " | " | C₁₉H₁₇ClO₄ | 344.78 | <50 | 44 | Cal. | 66.18 | 4.97 | — |
| | | | | | | | | Obt. | 66.27 | 5.13 | — |
| 12 | —CH—CH₂— | —OH | —O—CH₂—C₆H₄—CN | C₁₉H₁₇NO₄ | 323.33 | 135 | 21 | Cal. | 70.57 | 5.30 | 4.33 |
| | | | | | | | | Obt. | 70.53 | 5.07 | 4.43 |
| 13 A | " | —OCH₃ | " | C₂₀H₁₉NO₄ | 337.36 | 88 | 15 | Cal. | 71.20 | 5.68 | 4.15 |
| | | | | | | | | Obt. | 71.23 | 5.82 | 4.05 |
| 13 B | " | " | " | " | " | 96 | 26 | Cal. | 71.20 | 5.68 | 4.15 |
| | | | | | | | | Obt. | 71.47 | 5.64 | 4.10 |
| 13 | " | " | " | " | " | — | — | Cal. | 71.20 | 5.68 | 4.15 |
| | | | | | | | | Obt. | — | — | — |
| 14 | —C═CH— | " | " | C₂₀H₁₇NO₄ | 335.34 | 70 | 30 | Cal. | 71.63 | 5.11 | 4.18 |
| | | | | | | | | Obt. | 71.67 | 5.05 | 4.25 |
| 15 | —CH—CH₂— | " | —O—CH₂—pyridyl, oxalate | C₂₀H₂₁NO₈ | 403.38 | 110 | 23 | Cal. | 59.55 | 5.25 | 3.47 |
| | | | | | | | | Obt. | 59.27 | 5.23 | 3.39 |
| 16 | " | —OH | —O—CH₂—C₆H₃(NO₂)(CN) | C₁₉H₁₆N₂O₆ | 368.33 | 90 | 19 | Cal. | 61.95 | 4.38 | 7.61 |
| | | | | | | | | Obt. | 61.94 | 4.41 | 7.79 |

TABLE I-continued

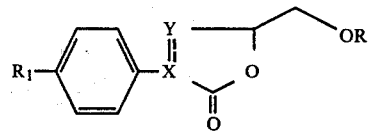

| Compound Code number | —X=Y— | —OR | —R₁ | Empirical formula | Molecular weight | Melting point (°C.) | Yield (%) | ELEMENTARY ANALYSIS | | C | H | N |
|---|---|---|---|---|---|---|---|---|---|---|---|---|
| 17 A | " | —OCH₃ | " | C₂₀H₁₈N₂O₆ | 382.36 | 117 | 7 | Cal. | | 62.82 | 4.75 | 7.33 |
|  |  |  |  |  |  |  |  | Obt. | | 63.09 | 4.60 | 7.56 |
| 17 B | " | " | " | " | " | 92 | 20 | Cal. | | 62.82 | 4.75 | 7.33 |
|  |  |  |  |  |  |  |  | Obt. | | 62.93 | 4.94 | 7.33 |
| 17 | " | " | " | " | " | — | — | Cal. | | 62.82 | 4.75 | 7.33 |
|  |  |  |  |  |  |  |  | Obt. | | — | — | — |
| 18 A | " | " | -O-CH₂-C₆H₃(Cl)(F) | C₁₉H₁₈ClFO₄ | 364.79 | 70 | 18 | Cal. | | 62.55 | 4.97 | — |
|  |  |  |  |  |  |  |  | Obt. | | 62.65 | 4.84 | — |
| 18 B | " | " | " | " | " | 76 | 18 | Cal. | | 62.55 | 4.97 | — |
|  |  |  |  |  |  |  |  | Obt. | | 62.81 | 4.76 | — |
| 18 | " | " | " | " | " | — | — | Cal. | | 62.55 | 4.97 | — |
|  |  |  |  |  |  |  |  | Obt. | | — | — | — |
| 19 | —C≡CH— | " | " | C₁₉H₁₆ClFO₄ | 362.77 | 78 | 56 | Cal. | | 62.90 | 4.45 | — |
|  |  |  |  |  |  |  |  | Obt. | | 62.71 | 4.32 | — |
| 20 | " | " | -O-CH₂-C₆H₅ | C₁₉H₁₈O₄ | 310.33 | 54 | 67 | Cal. | | 73.53 | 5.85 | — |
|  |  |  |  |  |  |  |  | Obt. | | 73.23 | 6.04 | — |

The compounds of formula (I) were studied on laboratory animals and showed activities in the psychotrope field, particularly as reversible inhibitors of monoamine oxidase.

These activities were brought out in the following tests:

Test A: Antagonism with respect to ptosis observed one hour after an intravenous injection (2 mg/kg) of reserpine given to mice according to the protocol described by GOURET C. and THOMAS J. in J. Pharmacol. (Paris, (1973), 4, 401.

Test B: Potentialization in mice of generalized trembling caused by an intraperitoneal injection of dl-5-hydroxytryptophane, according to the protocol described by GOURET C. and RAYNAUD G. in J. Pharmacol. (Paris), (1974), 5, 231.

Test C: The inhibiting activity of monoamine oxidase was measured on two rat brain homogenates at varying times after oral administration of a dose of 5 mg/kg of the compounds of formula (I). Type "A" activity was measured by using serotonine as substrate and that of type "B" by using phenylethylamine, according to the protocols described by R. J. WURTMAN and J. AXELROD in J. Biol. Chem. 241, 2301, (1966), and J. A. ROTH and C. N. GILLIS in Mol. Pharmacol. 11, 28–35, (1975).

The results obtained in these three tests with the compounds of formula (I) as well as those obtained with reference substances are shown in tables II and III below.

TABLE II

| | TEST A - TEST B | | |
|---|---|---|---|
| Compound code number | Acute toxicity LD 50 (mg/kg/p.o.) (mice) | Test A ED 50 (mg/kg/p.o.) | Test B ED 50 (mg/kg/p.o.) |
| 1 | — | 19 | 14 |
| 2 | >2000 | 5.5 | 9 |
| 3 B | 2000 | 3.6 | 1.7 |
| 4 | >2000 | 0.3 | 0.19 |
| 5 B | — | 11.5 | 15.5 |
| 6 | — | 1.4 | 1.5 |
| 6 A | >2000 | 4.4 | 5.8 |
| 6 B | >2000 | 1.6 | 2 |
| 7 A | — | 12.5 | 10 |
| 7 B | >2000 | 2.5 | 3.2 |
| 8 A | >2000 | 6.2 | 4.4 |
| 8 B | 2000 | 0.58 | 0.29 |
| 9 | >2000 | 0.22 | — |
| 10 A | >2000 | 24 | 10 |
| 10 B | >2000 | 15 | 10 |
| 11 | >2000 | 2.3 | 1.6 |
| 12 | — | 10 | 16 |
| 13 A | >2000 | 12 | 20 |
| 13 B | >2000 | 0.9 | 1.7 |

TABLE II-continued

TEST A - TEST B

| Compound code number | Acute toxicity LD 50 (mg/kg/p.o.) (mice) | Test A ED 50 (mg/kg/p.o.) | Test B ED 50 (mg/kg/p.o.) |
|---|---|---|---|
| 14 | — | 0.68 | 0.55 |
| 15 | — | 5.8 | 12 |
| 16 | >2000 | 1.2 | 3.5 |
| 17 A | >2000 | 5.5 | 6.4 |
| 17 B | 1700 | 0.32 | 0.55 |
| 18 A | — | 23 | 16 |
| 18 B | >2000 | 5.4 | 3.1 |
| 19 | >2000 | 2.1 | 2.4 |
| 20 | >2000 | 4.4 | 4 |
| NIALAMIDE | 1100 | 4.5 | 5.2 |
| DEPRENYL | 520 | 9 | 3 |
| TRANYLCYPROMINE | 58 | 1.55 | 1.37 |
| PARGYLINE | 480 | 34 | 48 |

TABLE III

TEST C

| Compound code number | Dose (mg/kg/p.o.) | Activity IMAO "A" Max | 8 hrs | 24 hrs | Activity IMAO "B" Max | 8 hrs | 24 hrs |
|---|---|---|---|---|---|---|---|
| 6 B | 5 | 83 | 12 | 0 | 17 | 2 | 0 |
| 8 B | 5 | 89 | 40 | 0,5 | 35 | 11 | 3 |
| 10 A | 5 | 27 | 11 | 4 | 79 | 40 | 4 |
| 10 B | 5 | 68 | 39 | 2 | 82 | 62 | 8 |
| 13 B | 5 | 91 | 43 | 3 | 23 | 7 | 4 |
| 4 | 5 | 90 | 45 | 0 | 8 | 8 | 0 |
| 6 | 5 | 87 | 20 | 1 | 22 | 13 | 3 |
| 17 B | 5 | 95 | 86 | 27 | 17 | 2 | 0 |
| 18 A | 5 | 21 | 11 | 5 | 80 | 58 | 16 |
| 18 B | 5 | 62 | 21 | 2 | 90 | 70 | 12 |
| 13 A | 5 | 51 | 26 | 2 | 11 | 7 | 0 |
| 9 | 5 | 97 | 80 | 26 | 83 | 32 | 3 |
| 11 | 5 | 80 | 34 | 1 | 96 | 81 | 15 |
| 19 | 5 | 72 | 49 | 16 | 97 | 92 | 48 |
| 14 | 5 | 97 | 68 | 0 | 71 | 22 | 0 |
| NIALAMIDE | 5 | Inactive | | | Inactive | | |
| TRANYLCYPROMINE | 5 | 88 | 65 | 67 | 100 | 76 | 84 |
| DEPRENYL | 5 | 10 | 0 | 0 | 85 | 71 | 63 |
| PARGYLINE | 5 | 8 | 6 | 7 | 72 | 72 | 70 |

As the results given in tables II and III show, the difference between the toxic doses and the active doses allows the compounds of formula (I) to be used in therapeutics as inhibitors of monoamine oxidase; they will be used in particular as antidepressives and in cerebral deficiency pathologies of old age.

They will be preferably administered orally with a physiologically acceptable excipient in the form of tablets, pills or capsules, at a dosage not exceeding 500 mg/day of active substance, or in the form of an injectable solute at a dosage not exceeding 50 mg/day of active substance; the solvent used is formed from binary and ternary mixtures containing, for example water, propylene glycol, polyethylene glycol 300 or 400 or any other physiological solvent, the relative proportions of the different constituents being adjusted with respect to the dose administered. Finally, it should be noted that said tablets, pills, capsules and injectable solutions may contain one or more compounds of formula (I) of the invention.

We claim:

1. A compound having the formula

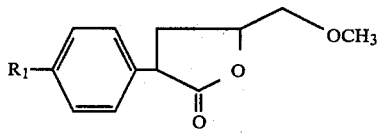

wherein $R_1$ is selected from the group consisting of 4-chlorobutoxy, 4-cyanobutoxy, benzyloxy, meta-nitrobenzyloxy, meta-chlorobenzyloxy, meta-cyanobenzyloxy, 3-pyridinylmethoxy, 3-cyano-5-nitrobenzyloxy and 3-chloro-4-fluorobenzyloxy, as a mixture of four diastereoisomers thereof, a mixture of two cis diastereoisomers thereof or a mixture of two trans diastereoisomers thereof, with the exception that a mixture of two trans diastereoisomers is excluded when $R_1$ is 4-chlorobutoxy or benzyloxy and that a mixture of two cis diastereoisomers and a mixture of two trans diastereoisomers are excluded when $R_1$ is 4-cyanobutoxy or 3-pyridinylmethoxy.

2. A mixture of two cis diastereoisomers of compound as claimed in claim 1, wherein $R_1$ is

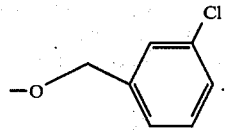

3. A mixture of two trans diastereoisomers of compound as claimed in claim 1, wherein $R_1$ is

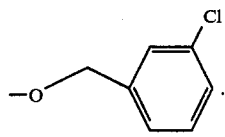

4. A mixture of four diastereoisomers of compound as claimed in claim 1, wherein $R_1$ is

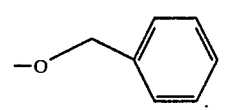

5. A mixture of four diastereoisomers of compound as claimed in claim 1, wherein $R_1$ is $-O-(CH_2)_4-CN$.

6. A mixture of two cis diastereoisomers of compound as claimed in claim 1, wherein $R_1$ is

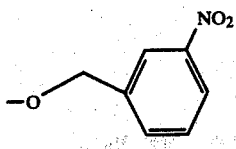

7. A mixture of two cis diastereoisomers of compound as claimed in claim 1, wherein $R_1$ is

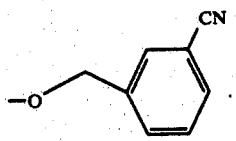

8. A mixture of two cis diastereoisomers of compound as claimed in claim 1, wherein $R_1$ is

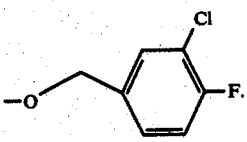

9. A pharmaceutical composition for treating subjects suffering from depression comprising a pharmacologically effective amount of compound as claimed in claim 1, in combination with a pharmacologically acceptable carrier.

* * * * *